US008608328B2

(12) United States Patent
Panagotacos et al.

(10) Patent No.: US 8,608,328 B2
(45) Date of Patent: Dec. 17, 2013

(54) LIGHT SOURCE WITH SECONDARY EMITTER CONVERSION ELEMENT

(75) Inventors: George W. Panagotacos, Corona, CA (US); David G. Pelka, Los Angeles, CA (US)

(73) Assignee: Teledyne Technologies Incorporated, Thousand Oaks, CA (US)

( * ) Notice: Subject to any disclaimer, the term of this patent is extended or adjusted under 35 U.S.C. 154(b) by 236 days.

(21) Appl. No.: 13/102,580

(22) Filed: May 6, 2011

(65) Prior Publication Data

US 2012/0281389 A1    Nov. 8, 2012

(51) Int. Cl.
*F21V 9/16* (2006.01)
*F21V 9/00* (2006.01)

(52) U.S. Cl.
USPC ............................................. 362/84; 313/501

(58) Field of Classification Search
USPC ................... 362/84, 97.2–97.3; 313/501, 506
See application file for complete search history.

(56) References Cited

U.S. PATENT DOCUMENTS

| | | |
|---|---|---|
| 6,560,038 B1 | 5/2003 | Parkyn, Jr. et al. |
| 7,267,787 B2 | 9/2007 | Dong et al. |
| 7,663,152 B2 | 2/2010 | Bierhuizen et al. |
| 7,671,529 B2 | 3/2010 | Mueller et al. |
| 7,682,850 B2 | 3/2010 | Harbers et al. |
| 7,703,943 B2 | 4/2010 | Li et al. |
| 7,737,636 B2 | 6/2010 | Li et al. |
| 7,768,754 B2 | 8/2010 | Collins, III et al. |
| 7,830,434 B2 | 11/2010 | Li et al. |
| 7,845,839 B2 | 12/2010 | Collier |
| 2003/0235800 A1* | 12/2003 | Qadar ............................. 433/29 |
| 2007/0076414 A1* | 4/2007 | Holder et al. ................. 362/310 |
| 2007/0269611 A1 | 11/2007 | Xiang et al. |
| 2008/0029720 A1 | 2/2008 | Li |
| 2008/0130289 A1* | 6/2008 | Takemoto et al. ............ 362/294 |
| 2008/0192458 A1 | 8/2008 | Li |
| 2008/0218992 A1 | 9/2008 | Li |
| 2008/0252197 A1 | 10/2008 | Li et al. |
| 2008/0278927 A1 | 11/2008 | Li et al. |
| 2009/0101930 A1 | 4/2009 | Li |
| 2009/0117672 A1 | 5/2009 | Caruso et al. |
| 2009/0134414 A1 | 5/2009 | Li et al. |
| 2009/0168398 A1 | 7/2009 | Collier |
| 2009/0224652 A1 | 9/2009 | Li et al. |
| 2009/0262516 A1 | 10/2009 | Li |
| 2010/0052560 A1 | 3/2010 | Li et al. |
| 2010/0060130 A1 | 3/2010 | Li |
| 2010/0067216 A1 | 3/2010 | Li |
| 2010/0067217 A1 | 3/2010 | Li |
| 2010/0164346 A1 | 7/2010 | Li et al. |
| 2010/0181582 A1 | 7/2010 | Li et al. |
| 2010/0188839 A1 | 7/2010 | Li |

(Continued)

*Primary Examiner* — Karabi Guharay
*Assistant Examiner* — Nathaniel Lee
(74) *Attorney, Agent, or Firm* — K&L Gates LLP

(57) ABSTRACT

A light source is disclosed. The light source includes a primary excitation source configured to emit electromagnetic radiation at a first peak wavelength and a band of wavelengths around the first peak wavelength. A secondary emitter conversion element is optically coupled to the primary excitation source and is configured to absorb at least a portion the electromagnetic radiation at the first peak wavelength from the primary excitation source and emit electromagnetic radiation at a second peak wavelength and a band of wavelengths around the second peak wavelength. The second peak wavelength is longer than the first peak wavelength. A non-imaging optical coupler is optically coupled to the secondary emitter conversion element. An optical system includes the light source optically coupled to a transparent rod.

62 Claims, 4 Drawing Sheets

(56) References Cited

U.S. PATENT DOCUMENTS

| | | |
|---|---|---|
| 2010/0188867 A1 | 7/2010 | Li |
| 2010/0237760 A1 | 9/2010 | Yang |
| 2010/0295070 A1 | 11/2010 | Su et al. |
| 2010/0295077 A1 | 11/2010 | Melman |
| 2010/0295078 A1 | 11/2010 | Chen et al. |
| 2010/0295079 A1 | 11/2010 | Melman |
| 2010/0321919 A1 | 12/2010 | Yang |
| 2010/0328926 A1* | 12/2010 | Hoelen et al. .................. 362/84 |

* cited by examiner

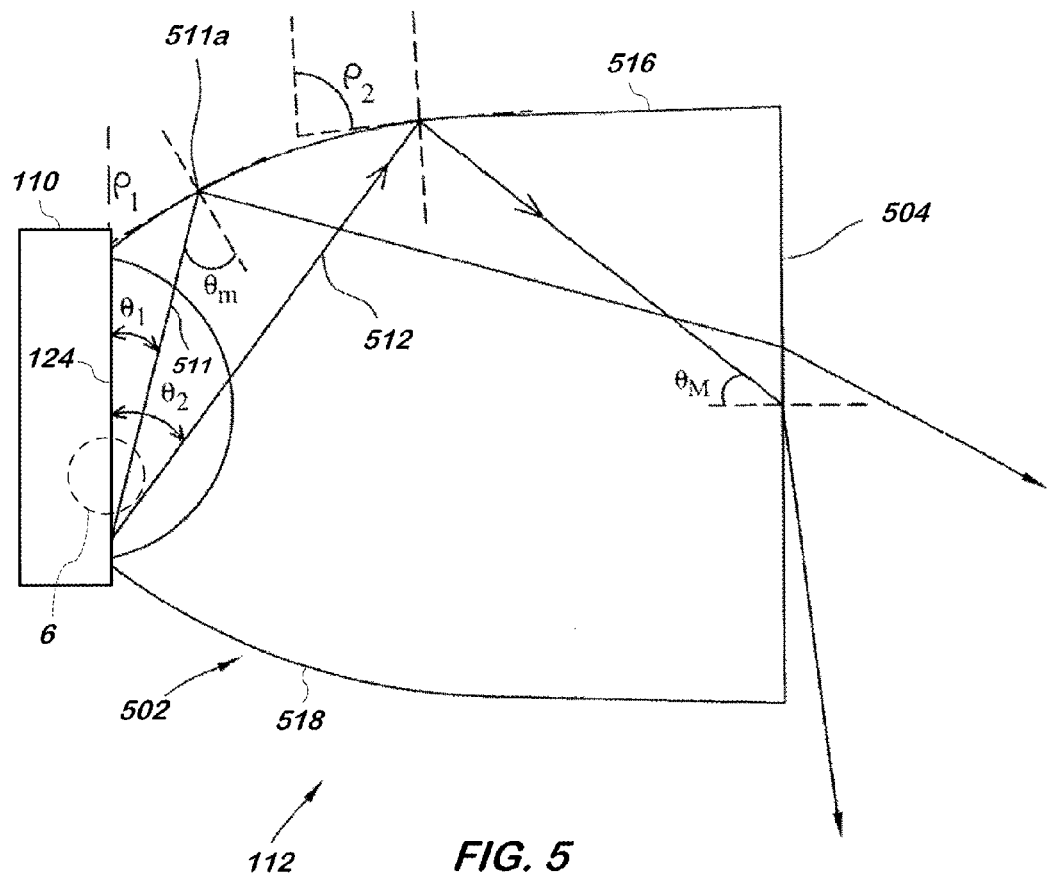
FIG. 5
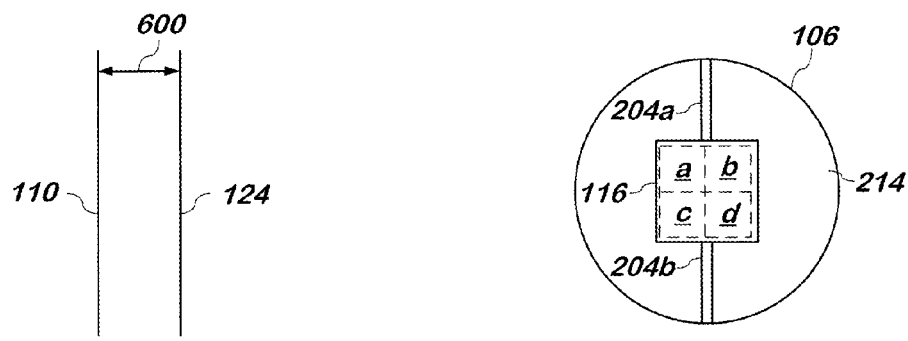
FIG. 6
FIG. 8

LIGHT SOURCE WITH SECONDARY EMITTER CONVERSION ELEMENT

BACKGROUND

Light emitting devices including light emitting diodes (LEDs) are well known solid devices that generate light having a peak wavelength in a specific region of the light spectrum. LEDs are typically used as illuminators, indicators, and displays. LEDs have been developed to emit light in a relatively narrow band around a peak wavelength. Light having a first peak wavelength ("primary light") can be converted into light having a longer peak wavelength ("secondary light") using a process known as luminescence. The luminescent process involves absorbing the primary light by a photoluminescent phosphor material, which excites the atoms of the phosphor material, and emits the secondary light. The peak wavelength, and the band of wavelengths around the peak wavelength, of the secondary light will depend on the phosphor material.

High flux density solid state light generators are now used in many applications to replace conventional light sources. Some conventional high flux density solid state light generators use light radiation emitted by LED elements in dice form (integrated circuit chips) directly. In many applications, high flux density light generators require very specific peak wavelength emission by the primary light source. Currently, LEDs can only supply peak wavelengths in the spectral bands of 420-460 nm, 520-540 nm, 620-660 nm, and a phosphor converted false white spectrum made from combining blue LEDs with a YAG (Yttrium, Aluminum, and Garnett) phosphor. It has been difficult, however, to maintain a constant correlated color temperature radiation from LED light sources.

Phosphorescent LEDs have a luminescent phosphor coating applied on top of a light emitting surface of the LED die. Generally, however, it is difficult to apply the luminescent phosphor coating uniformly on the die such that the primary light emitted from the LED has the same constant correlated color temperature, e.g., the same warmness, as a function of angle. A varying correlated color temperature is manifested when viewing the LED straight on and then from a wide angle of 80° or 90°. When viewed head on, the light will appear to have one color temperature, but when viewed from a greater angle, 80° or 90° angle from straight on, the light will appear to have another color temperature. Thus, conventional luminescent phosphor (phosphorescent) LEDs cannot produce a constant correlated color temperature radiation.

SUMMARY

In one embodiment, a light source is provided. The light source comprises a primary excitation source configured to emit electromagnetic radiation at a first peak wavelength. A secondary emitter conversion element is optically coupled to the primary excitation source and is configured to absorb at least a portion the electromagnetic radiation at the first peak wavelength from the primary excitation source and emit electromagnetic radiation at a second peak wavelength. The second peak wavelength is longer than the first peak wavelength. A non-imaging optical coupler is optically coupled to the secondary emitter conversion element.

FIGURES

FIG. 5 is a cross-sectional view of an optical coupler portion of the light source shown in FIG. 1.

FIG. 6 illustrates one embodiment of the light source shown in FIG. 1 where a gap is provided between the output surface of a secondary emitter conversion element and an input surface of a non-imaging optical coupler.

FIG. 8 is a top view of a substrate comprising a primary excitation source.

DESCRIPTION

Figure 1:
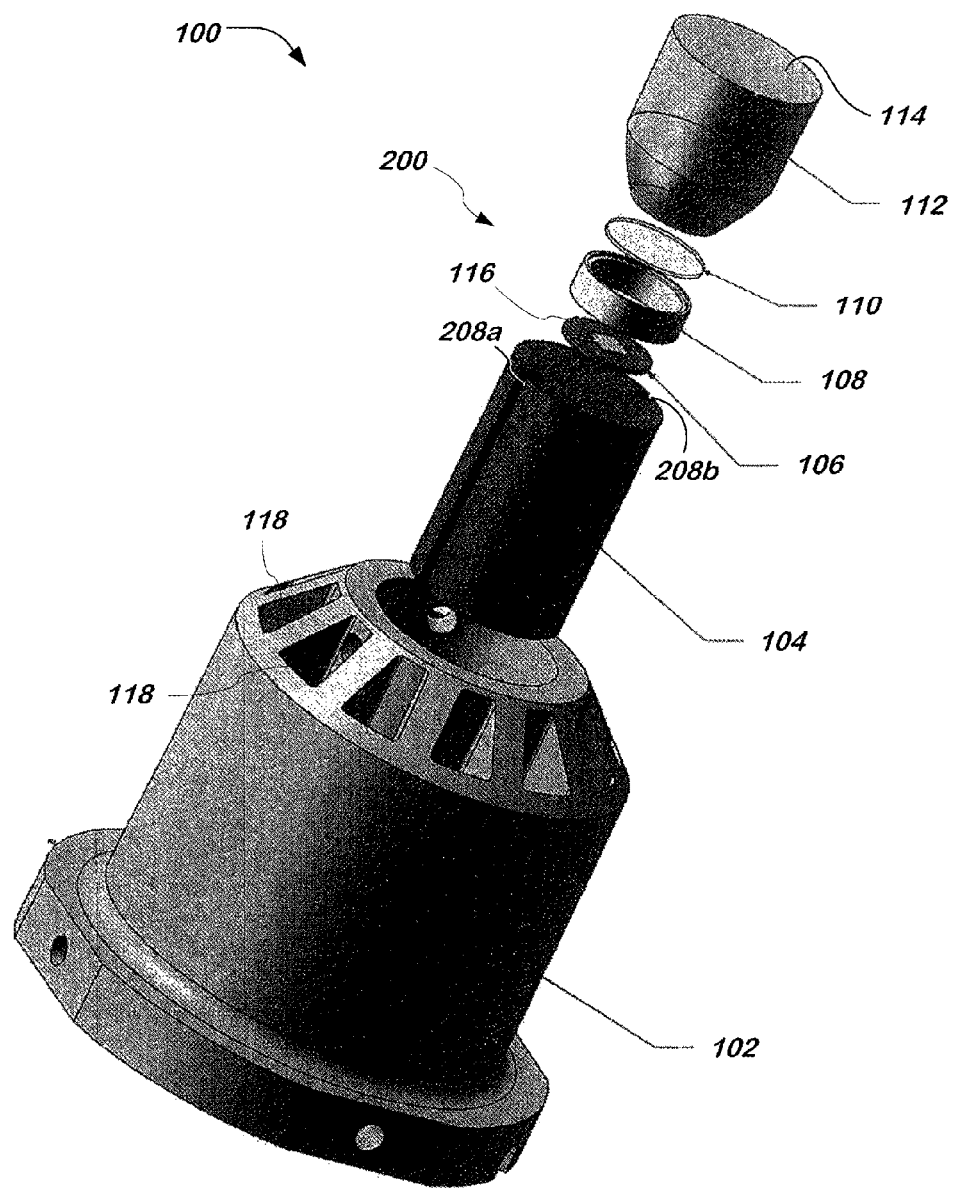
FIG. 1 is an exploded view of an inner assembly of one embodiment of a light source that employs a secondary emitter conversion element.

Before explaining the various embodiments in detail, it should be noted that the embodiments are not limited in their application or use to the details of construction and arrangement of elements illustrated in the accompanying drawings and description. The illustrative embodiments may be implemented or incorporated in other embodiments, variations and modifications, and may be practiced or carried out in various techniques. Features or elements described with respect to one embodiment may be incorporated in other embodiments. Embodiments and configurations of the disclosed light source and in particular the high flux density light generator that employs a secondary emitter using a phosphor conversion element apparatus and system disclosed herein are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

As used herein the term radiant electromagnetic energy refers to light in the visible and invisible spectrum including light at a peak wavelength, and the band of wavelengths around the peak wavelength, ranging from the ultraviolet (UV, e.g., less than 380 nm) to the infrared (IR, e.g., longer than 750 nm) range. Accordingly, the terms optics and/or optical refers generally to the behavior of light in the visible and invisible spectrum including peak wavelengths from the ultraviolet to the infrared range. Because light is an electromagnetic wave, other forms of electromagnetic radiation such as X-rays, microwaves, and radio waves exhibit similar properties.

In one general aspect, the disclosed embodiments are directed generally to a light source. In one embodiment, the light source comprises a primary excitation source configured to emit electromagnetic radiation at a first peak wavelength and a band of wavelengths around the peak wavelength (in short "peak wavelength"). A secondary emitter conversion element is configured to absorb at least a portion the electromagnetic radiation at the first peak wavelength from the primary excitation source and emit electromagnetic radiation at a second peak wavelength. The second peak wavelength is longer than the first peak wavelength. A non-imaging optical (NIO) coupler is optically coupled to the secondary emitter conversion element. The electromagnetic radiation emitted by the primary excitation source is absorbed at least partially by a first surface (input surface) of the secondary emitter conversion element and in response the secondary emitter conversion element emits electromagnetic radiation from both the first surface and a second surface (output surfaces). The radiation emitted from the second surface of the secondary conversion emitter element is at least partially optically coupled to the NIO coupler. The radiation emitted from the first surface of the secondary emitter conversion element is at least partially reflected by a reflective surface of a substrate back into the first surface of the secondary emitter conversion element.

In one aspect, the disclosed embodiments are directed to a high flux density light source comprising a primary excitation source and a secondary emitter conversion element. The secondary emitter conversion element comprises a ceramic substrate having a first input surface and first and second output surface(s). The secondary emitter conversion element receives radiation at a first peak wavelength from the primary excitation source at the first input surface, at least partially absorbs the radiation at the first peak wavelength, and emits radiation at a second peak wavelength from the first and second output surface(s). In one embodiment, the second peak wavelength is longer than the first peak wavelength. In one embodiment, the high flux density light source is configured as a white light high flux density light source. In such embodiments, the excitation source comprises a UV or blue LED element or an array of UV or blue LED elements configured to emit radiation at a first peak wavelength. The secondary ceramic emitter conversion element at least partially absorbs the radiation emitted by the primary excitation source at the first input surface and wavelength shifts the radiation absorbed at the first input surface and emits radiation from the first and second output surfaces to a highly consistent correlated color temperature white light source. It will be appreciated that in the embodiments illustrated herein, the first output surface of the secondary ceramic emitter conversion element is the same of the first input surface of the secondary ceramic emitter conversion element. In other embodiments, the first input surface and the first output surface are not necessarily the same. The radiation emitted from the second output surface of the secondary ceramic emitter conversion element and closest to the input surface of the NIO coupler is entrained by a NIO element to produce radiation within an acceptance angle of a large core waveguide into which it may be coupled for distribution purposes. In one embodiment, the NIO coupler only sees the radiation emitted from the second output surface of the secondary ceramic emitter conversion element. The radiation emitted from the first output surface of the secondary ceramic emitter conversion element is at least partially reflected by a reflective surface of a substrate.

In one aspect, the disclosed embodiments are directed to a high flux density light source configured as a false white photon engine comprising one or an array of UV or blue LED elements placed on a specular or diffusive reflective substrate (specular and/or diffusive reflective substrates may be employed that have at least a 90% reflectivity and more preferably a 95% reflectivity) of very low thermal resistance and excited by a constant current, typically of between 350 mA to 1500 mA. Such UV or blue LED elements then have their emitted light impinge upon a ceramic phosphor element, which absorbs the shorter peak wavelength light radiated by the UV or blue LED elements and via a Stoke's shift, re-emits the light at a longer peak wavelength in a visible portion of the spectrum (i.e., white light portion of the spectrum). A reflective cavity ring-like assembly is placed between the LED excitation source and the ceramic phosphor conversion element's first input surface to keep light rays emitted at tangential angles of incidence from escaping the system and consequently reducing the overall optical efficiency of the whole system. Finally light emitted from the ceramic phosphor conversion element is collected and collimated via a rotationally symmetric NIO element (e.g., coupler) that is configured to match the numerical aperture of the large-core waveguide to which the high-density flux source may be eventually attached to.

FIG. 1 is an exploded view of an inner assembly of one embodiment of a light source 100 that employs a secondary emitter conversion element. In one embodiment, the light source 100 may be employed as a high flux density light generator. In the embodiment illustrated in FIG. 1, the light source 100 comprises a housing 102 and a photon engine 200 that is contained within the housing 100. In one embodiment, the photon engine 200 comprises a primary excitation source 116, a secondary emitter conversion element 110 optically coupled to the primary excitation source 116, and a NIO coupler 112 optically coupled to the secondary emitter conversion element 110, with or without an air-gap between the second surface of the ceramic conversion element 110 and the input surface of the NIO coupler 112. The primary excitation source 116 is configured to emit electromagnetic radiation at a first peak wavelength. As previously discussed, throughout this disclosure, the peak wavelength is short for peak wavelength and a band of wavelengths around the peak wavelength. The secondary emitter conversion element 110 is configured to absorb at least a portion the electromagnetic radiation at the first peak wavelength from the primary excitation source 116 and emit electromagnetic radiation at a second peak wavelength. The second peak wavelength is longer (or higher) than the first peak wavelength. The NIO coupler 112 is configured to optically couple to a large core waveguide. In one aspect, the large core waveguide may be formed of an optical bundle and have a diameter of about 5 mm to about 10 mm, for example.

In one embodiment, the primary excitation source 116 comprises a solid state excitation source and, in one embodiment, the primary excitation source 116 may be positioned on a substrate 106. The primary excitation source 116 may comprise at least one LED element or an array of LED elements. For example, the primary excitation source 116 may comprise a single LED or may comprise an array of multiple (two or more) LED elements. The at least one LED may be configured to emit electromagnetic radiation at a first peak wavelength, wherein the first peak wavelength falls in the range of about 365 nm to about 465 nm and the wherein the secondary emitter conversion element 110 is configured to emit electromagnetic radiation at a second wavelength, wherein the second peak wavelength falls in the range of about 415 nm to about 705 nm. Other suitable peak wavelength combinations may be employed based on the characteristic of the secondary emitter conversion element 110 provided that the second peak wavelength is longer than the first peak wavelength. For example, the second peak wavelength may be about 50 nm to about 60 nm, or more, longer than the first peak wavelength.

Figure 2:
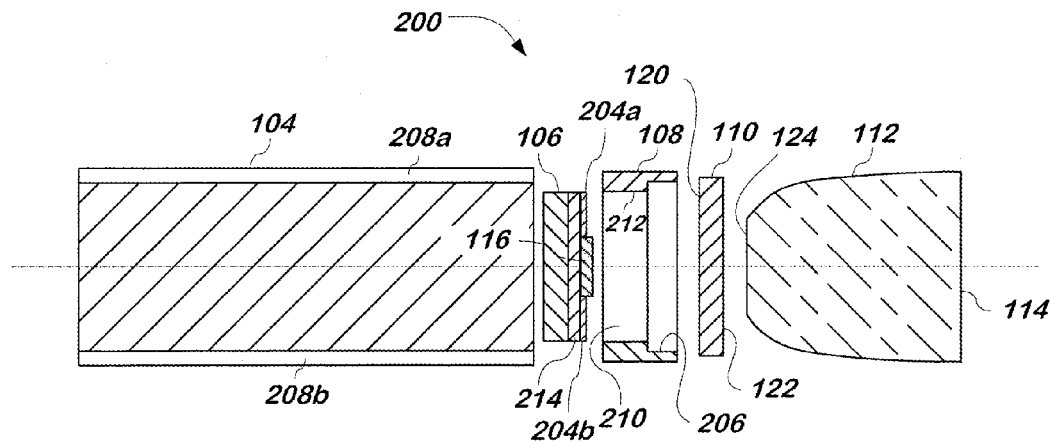
FIG. 2 is a cross-sectional view of a photon engine portion of the light source shown in FIG. 1

In one embodiment, the secondary emitter conversion element 110 comprises a ceramic substrate having an input surface (e.g., first surface) and at least two output surfaces (e.g., first and second surfaces). The secondary emitter conversion element 110 absorbs the radiation emitted by the primary excitation source 116 at the input surface and wavelength shifts the radiation received at the input surface and emits radiation from the output surfaces to a highly consistent correlated color temperature white light source. The radiation emitted from one of the output surfaces (the second surface 122 of the secondary conversion emitter 110 as shown in FIG. 2, for example) of the secondary emitter conversion element 110 is entrained by the NIO element 112 to produce radiation from an output surface 114 (or exit face) within an acceptance angle of a large core waveguide into which it may be coupled for distribution purposes.

In one embodiment, the secondary emitter conversion element 110 may comprise a ceramic substrate that has a phosphorescent material applied thereon. In one embodiment, the secondary emitter conversion element 110 may comprise a ceramic substrate comprising LED phosphor materials such as those provided by Internatix of Fremont, Calif. Such LED phosphors provide blue light down selection access to the entire color spectrum, regardless of the type of underlying UV or blue LED die (chip). The Internatix materials provide uniform light output at the desired color rendering index (CRI) and correlated color temperature (CCT), without being impacted by the variations in light output from LED die to die or from manufacturer to manufacturer. It will be appreciated that the CRI (sometimes called color rendering index), is a quantitative measure of the ability of a light source to reproduce the colors of various objects faithfully in comparison with an ideal or natural light source. Light sources with a high CRI are desirable in color-critical applications such as photography and cinematography. It is defined by the International Commission on Illumination as color rendering, e.g., effect of an illuminant on the color appearance of objects by conscious or subconscious comparison with their color appearance under a reference illuminant. The CRI of a light source does not indicate the apparent color of the light source; that information is under the rubric of the correlated color temperature (CCT).

In one embodiment, a reflective optical cavity 108 is provided to receive therein the secondary emitter conversion element 110 and transmit substantially all of the light from the primary excitation source 116 to the input surface of the secondary emitter conversion element 110. In one embodiment, the reflective optical cavity 108 is configured to receive the secondary emitter conversion element 110. For example, the reflective optical cavity 108 may comprise a seat 206 (FIG. 2) to receive the secondary emitter conversion element 110. In the embodiment illustrated in FIG. 1, the reflective optical cavity 108 has a cylindrical shape and the secondary emitter conversion element 110 has a circular shape (disk). It will be appreciated that other geometric mating configurations may be employed such as square, rectangular, rhomboidal, triangular, elliptical, or any other suitable shape for the secondary emitter conversion element 110 as well as the corresponding reflective optical cavity 108.

In one embodiment, an inner surface of the reflective optical cavity 108 may have a sidewall shape having a curvature. In one embodiment, the curvature may be paraboloidal (e.g., in the form of a parabola or paraboloid) and in other embodiments the curvature may be elliptical. The curvature, e.g., parabolodial or elliptical, will reflect the incoming light from the primary excitation source 116 such that it exits at an angle of substantially less than 90°. Thus, when the incoming light rays hit the curved inner sidewall surface it will be transmitted in one reflection to the secondary emitter conversion element 110 superstrate located above it.

In various other embodiments, the inner surface of the reflective optical cavity 108 may have a reflective finish or coating formed thereon. In various aspects, the reflective finish or coating on the inner sidewall surface of the reflective optical cavity 108 may be specular or diffuse reflective. A specular surface, e.g., a mirrored surface, has a reflectivity in excess of about 90% to over about 95%. A white diffused cavity, for example, has a diffused reflectivity in excess of about 90% to over about 95%. A reflectorized smooth mirror coating inside the reflective optical cavity 108 may be made out of aluminum or silver. These would be typical coatings on the inside sidewall of the reflective optical cavity 108.

In one embodiment, the photon engine 200 comprises a heat transfer element 104 thermally coupled to a substrate 106. The substrate 106 is configured to receive the primary excitation source 116 on a surface thereof. The primary excitation source 116 is electrically coupled to an energy source (not shown) by way of electrical conductive elements 204a and 204b. The electrical conductive elements 204a, 204b may be routed via channels 208a, 208b (or slots) formed within the heat transfer element 104 to prevent pinching the electrical conductive elements 204a, 204b between an outer wall of the heat transfer element 104 and an inner wall of the housing 104. In one embodiment, the substrate 106 may be reflective or diffusive (reflective and/or diffusive substrates may be employed that have at least a 90% reflectivity and more preferably a 95% reflectivity). In operation, the primary excitation source 116 may draw of between about 350 mA to about 1500 mA and dissipate about 20 to about 40 Watts of power. Thus, the primary excitation source 116 generates heat that must be removed in order for the light source 100 to operate efficiently. In one embodiment, the reflective substrate 106 receives the light source 116 in the form of one or more semiconductor devices in die form. As the semiconductor devices heat up during operation, they output less light and become less efficient. The heat transfer element 104 (core) provides a medium for transferring the heat generated by the semiconductor die (or dice) to the heat transfer element 104 to reduce the thermal resistance of the primary excitation source 116. In various embodiments, the heat transfer element 104 may comprise copper (Cu), aluminum (Al) or any other material with suitable thermal transfer properties to adequately remove heat generated by the primary excitation source 116. In one embodiment, the housing 102 may be made of aluminum and forms a portion of the heat convection mechanism. In one embodiment, the housing 102 may comprise a built-in fan or other ventilation mechanism. As shown in FIG. 1, the housing 104 comprises ventilation apertures 118 for heat convention purposes.

In one embodiment, a gap may be provided between the second output surface of the secondary emitter conversion element 110 and the input surface of the NIO coupler 112. In one aspect, the gap may be in the range of about 250 μm to about 500 μm. In another aspect, a material, such as, for example, optical grade Silicone may be disposed in the gap. In yet other embodiments, the gap between the second output surface of the secondary emitter conversion element 110 and the input surface of the NIO coupler 112 may be omitted altogether.

In one embodiment, the primary excitation source 116 may be configured to radiate light at a first peak wavelength. It will be appreciated by those skilled in the art that the primary excitation source 116 may comprise one or more LED elements that, when energized by an electrical power source may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may referred to as visible light or simply light. A typical human eye will respond to peak wavelengths in air from about 380 nm to about 750 nm. The visible spectrum is continuous and without clear boundaries between one color and the next. The following ranges of peak wavelengths may be used as an approximation of color wavelength:

Violet: about 380 nm to about 450 nm;
Blue: about 450 nm to about 495 nm;

Green: about 495 nm to about 570 nm;
Yellow: about 570 nm to about 590 nm;
Orange: about 590 nm to about 620 nm; and
Red: about 620 nm to about 750 nm.

The invisible spectrum (i.e., non-luminous spectrum) is that portion of the electromagnetic spectrum lies below and above the visible spectrum (e.g., below about 380 nm and above about 750 nm). The invisible spectrum is not detectable by the human eye. Peak wavelengths longer than about 750 nm are longer than the red visible spectrum and they become invisible infrared, microwave, and radio electromagnetic radiation. Wavelengths less than about 380 nm are shorter than the violet spectrum and they become invisible ultraviolet, x-ray, and gamma ray electromagnetic radiation. It will be appreciated that the secondary emitter conversion element materials should be selected such that the wavelength of the radiation output by the secondary emitter conversion element is longer then the wavelength of the radiation generated by the primary excitation source. As discussed above, the difference between the first and second peak wavelengths may be about 50 nm to about 60 nm or longer.

FIG. 2 is a cross-sectional view of a photon engine 200 portion of the light source 100 shown in FIG. 1. As shown in FIG. 2, the heat transfer element 104 is positioned to receive the substrate 106 comprising the primary excitation source 116 and is thermally coupled to the substrate 106. The primary excitation source 116 is electrically coupled to an energy source (not shown) by way of electrical conductive elements 204a and 204b. Such electrical conductive elements 204a, 204b are coupled to the primary excitation source 116 at one end to the energy source at the other end. The electrical conductive elements 204a, 204b may be routed via channels 208a, 208b (or slots) formed within the heat transfer element 104 to prevent pinching the electrical conductive elements 204a, 204b between an outer wall of the heat transfer element 104 and an inner wall of the housing 104 (FIG. 1).

The primary excitation source 116 is configured to be positioned within, partially within, or to illuminate an aperture 210 defined by the inner walls of the reflective optical cavity 108. In the embodiment, illustrated in FIG. 2, the reflective optical cavity 108 comprises inner walls 212 having a substantially cylindrical shape. The reflective optical cavity 108 also comprises a seat 206 to receive the secondary emitter conversion element 110. In one embodiment, the secondary emitter conversion element 110 comprises a first "input" surface 120 to receive radiation emitted by the primary excitation source 116 and first and second "output" surfaces 120 (first surface), 122 (second surface). It will be appreciated that in the embodiment illustrated in FIG. 2 the first input surface 120 and the first output surface 120 happen to correspond to the same surface. In other embodiments, the first input surface and the first output surface of the secondary emitter conversion element 110 are not necessarily the same. The radiation emitted from the second output surface 122 output is optically coupled to an input surface 124 of the NIO coupler 112. The light emitted from the second output surface 122 of the secondary emitter conversion element 110 enters the input surface 124 of the optically transparent body of the NIO coupler 112 and is totally internally reflected within the optically transparent body of the NIO coupler 112 and exits from the output surface 114. The light emitted from the first output surface 120 of the secondary emitter conversion element 110 is reflected by a reflective surface 214 of the substrate 106.

FIG. 8 is a top view of the substrate 106 comprising the primary excitation source 116, the reflective surface 214, and the electrical conductive elements 204a and 204b. In one embodiment, the excitation source 116 comprises at least one solid state light source (e.g., LED die). In other embodiments, the excitation source 116 comprises multiple light sources. For example, as shown in phantom in FIG. 8, the excitation source 116 may comprise four solid state light sources a, b, c, d (e.g., LED dice).

Figure 3:
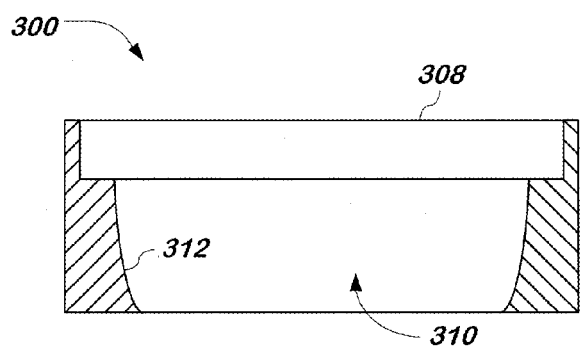
FIG. 3 is a cross-sectional view of one embodiment of a parabolic reflective cavity element.

Turning back now to FIG. 3, where a cross-sectional view 300 is shown of one embodiment of a parabolic reflective cavity element 308. As shown, the reflective optical element 308 comprises inner walls 312 having a substantially paraboloidal shape. Accordingly, the aperture 310 provides different reflective properties for reflecting the radiation received from the primary excitation source 116 than the cylindrical inner walls 212 of the reflective optical element 108 shown in FIG. 2.

Figure 4:
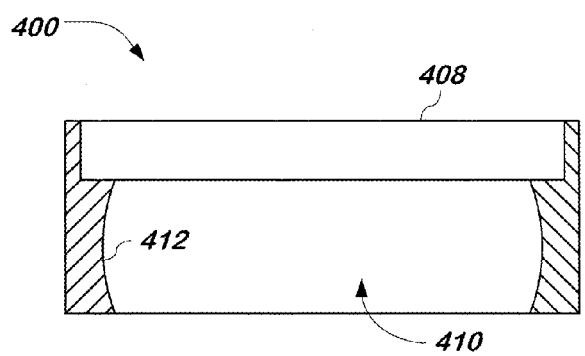
FIG. 4 is a cross-sectional view of one embodiment of an elliptical reflective cavity element.

FIG. 4 is a cross-sectional view 400 of one embodiment of an elliptical reflective cavity element 408. As shown, the reflective optical element 408 comprises inner walls 412 having a substantially elliptical shape. Accordingly, the aperture 410 provides different reflective properties for reflecting the radiation received from the primary excitation source 116 than the cylindrical inner walls 212 of the reflective optical element 108 shown in FIG. 2 or the paraboloidal inner walls 312 of the reflective optical element 308 shown in FIG. 3.

FIG. 5 is a cross-sectional view of an optical coupler 112 portion of the light source 100 shown in FIG. 1. The NIO coupler 112 is a figure of revolution combining a light-transmitting body 502 defining an input surface 124, the body 502 having a curved side wall 518 shaped to totally internally reflect all the light emitted from the secondary emitter conversion element 110, traveling toward the side wall 518. Within a predetermined distance from the input surface 124 of the body 502 having a cylindrical transition section 516 extending from the curved side wall 518 and forwardly. A planar output surface 114 is located at the forward end of the body 502, transverse to the central axis of the figure of revolution.

In one embodiment, the NIO coupler 112 enables coupling of light emitted from the secondary emitter conversion element 110 into a cylindrical light pipe or fiber optic waveguide, through which the light propagates to be emitted at its distal end, as discussed herein below in connection with FIG. 7. Still in FIG. 5, the NIO coupler 112 operates solely by total internal reflection and thus needs no mirror-coating.

As shown in FIG. 5, the NIO coupler 112, two exemplary rays 511 and 512, emitted from the radially outermost part of the input surface 124. The ray 511 makes angle $\theta_1$ with the input plane of the input surface 124, and strikes side wall 518 at a point 511a having slope angle $\rho_1$, which is determined so that the incidence angle equals $\theta_m$, slightly more than $\theta_c$, according to:

$$\rho_1 = \theta_1 - \theta_m + 90°$$

In FIG. 5, ray 512 makes angle $\theta_2$ with the plane of the input surface 124 and strikes the side wall 518 at a point having slope angle $\rho_2$, which is determined by having to reflect ray 512 onto the output surface 114 at an incidence angle equal to $\theta_M$, such that $$\rho_1 = (90° - \theta_2 - \theta_M)/2.$$

FIG. 6 illustrates one embodiment of the light source 100 shown in FIG. 1 where a gap is provided between an output surface of the secondary emitter conversion element 110 and an input surface of the NIO coupler 112. In one aspect, the gap 600 may be in the range of about 250 μm to about 500 μm. In another aspect, a material, such as, for example, optical grade Silicone may be disposed in the gap 600.

Figure 7:
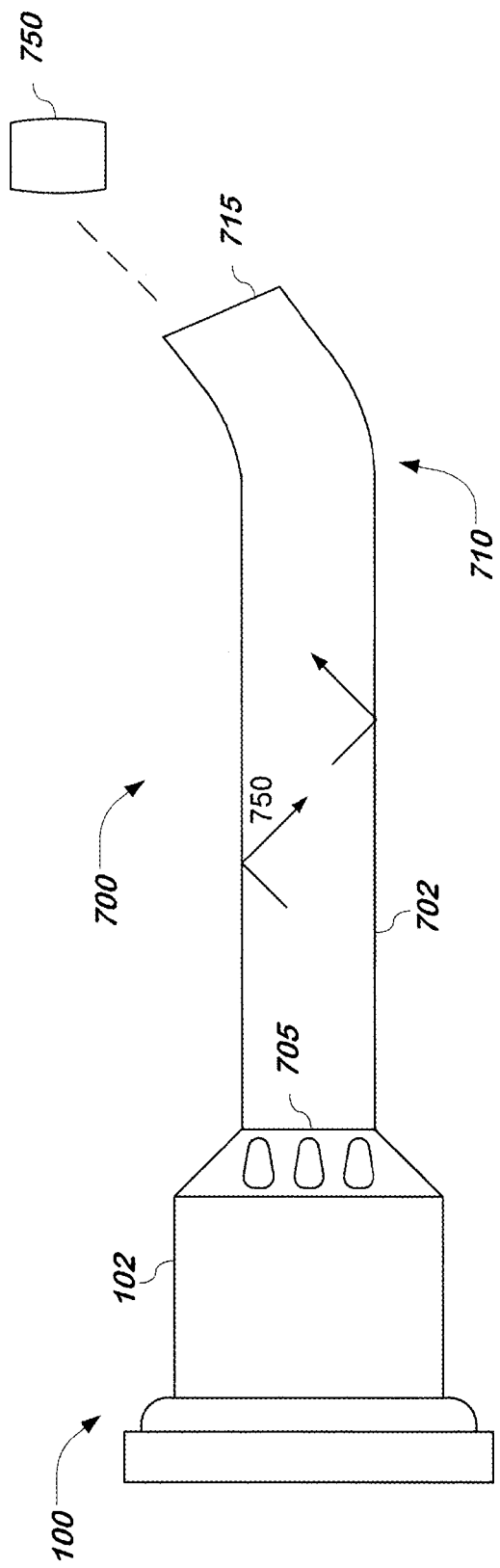
FIG. 7 illustrates one embodiment of an optical system comprising the light source shown in FIG. 1 coupled to a transparent rod.

FIG. 7 illustrates one embodiment of an optical system 700 comprising the light source 100 shown in FIG. 1 optically coupled to a transparent rod 702. FIG. 7 shows the light source coupler 100 coupled to the transparent rod 702, which may also be formed from a group of closely compacted plastic or glass fibers, is placed so that entry face 705 is juxtaposed to the output surface 114 of the NIO coupler 112, receiving its light output thereby. Typically the two end faces are in flat surface-to-surface engagement to exclude air gaps. The bend 710 portion of the transparent rod 602 is situated near the rod end 615, for convenience of application. Use for dental material curing, or dental whitening, is indicated schematically at 750, where 750 represents dental material being cured, or teeth being whitened. In other applications, the optical system 700 may be employed for spot curing epoxies or UV curing photoresist, UV printing, UV ink curing, fingerprint detection, for example.

Although the light source was illustrated and described herein as embodied in one or more specific examples, it is nevertheless not intended to be limited to the details shown. Various modifications and structural changes may be made therein without departing from the scope of the light source. Any modifications and structural changes are within the scope and range of equivalents of the claims. Accordingly, it is appropriate that the appended claims be construed broadly and in a manner consistent with the scope of the light source as set forth in the following claims.

The invention claimed is:

1. A light source, comprising:
 a primary excitation source configured to emit electromagnetic radiation at a first peak wavelength and a band of wavelengths around the first peak wavelength;
 a secondary emitter conversion element optically coupled to the primary excitation source, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
 a non-imaging optical coupler optically coupled to the secondary emitter conversion element; and
 a gap between the secondary emitter conversion element and the non-imaging optical coupler;
 wherein the gap is in the range of about 250 μm to about 500 μm.

2. The light source of claim 1, wherein the secondary emitter conversion element comprises a phosphor material.

3. The light source of claim 1, comprising:
 a reflective optical cavity configured to receive the secondary emitter conversion element.

4. The light source of claim 3, wherein the reflective optical cavity comprises a seat to receive the secondary emitter conversion element.

5. The light source of claim 3, wherein the reflective optical cavity has a cylindrical shape and the secondary emitter conversion element has a circular shape.

6. The light source of claim 3, wherein an inner surface of the reflective optical cavity has a paraboloidal shape.

7. The light source of claim 3, wherein an inner surface of the reflective optical cavity has an elliptical shape.

8. The light source of claim 3, wherein an inner surface of the reflective optical cavity has a specular reflectivity.

9. The light source of claim 3, wherein an inner surface of the reflective optical cavity has a diffuse reflectivity.

10. The light source of claim 1, comprising:
 a substrate to receive the primary excitation source, wherein the substrate comprises a reflective surface; and
 a heat transfer element thermally coupled to the substrate.

11. The light source of claim 1, wherein the primary excitation source comprises at least one light-emitting diode (LED).

12. The light source of claim 11, wherein the at least one LED is configured to emit electromagnetic radiation at the first peak wavelength, wherein the first peak wavelength falls in the range of about 365 nm to about 465 nm.

13. The light source of claim 11, wherein the secondary emitter conversion element is configured to emit electromagnetic radiation at the second peak wavelength, wherein the second peak wavelength falls in the range of about 415 nm to about 705 nm.

14. The light source of claim 1, comprising a material disposed in the gap.

15. The light source of claim 14, wherein the material is optical grade Silicone.

16. An optical system, comprising:
 a light source; and
 a transparent rod optically coupled to the light source;
 wherein the light source comprises:
 a primary excitation source configured to emit electromagnetic radiation at a first peak wavelength and a band of wavelengths around the first peak wavelength;
 a secondary emitter conversion element optically coupled to the primary excitation source, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
 a non-imaging optical coupler optically coupled to the secondary emitter conversion element; and
 a gap between the secondary emitter conversion element and the non-imaging optical coupler;
 wherein the gap is in the range of about 250 μm to about 500 μm.

17. The optical system of claim 16, wherein the secondary emitter conversion element comprises a phosphor material.

18. The optical system of claim 16, comprising:
 a reflective optical cavity configured to receive the secondary emitter conversion element.

19. A photon engine, comprising:
 a primary excitation source configured to emit electromagnetic radiation at a first peak wavelength and a band of wavelengths around the first peak wavelength;
 a secondary emitter conversion element optically coupled to the primary excitation source, the secondary emitter conversion element comprising a phosphor material, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
 a reflective optical cavity configured to receive the secondary emitter conversion element;
 a heat transfer element thermally coupled to the primary excitation source; and
 a non-imaging optical coupler optically coupled to the secondary emitter conversion element; and a gap between the secondary emitter conversion element and the non-imaging optical coupler;
wherein the gap is in the range of about 250 µm to about 500 µm.

20. The photon engine of claim 19, wherein the reflective optical cavity comprises a seat to receive the secondary emitter conversion element.

21. The photon engine of claim 19, wherein the reflective optical cavity has a cylindrical shape and the secondary emitter conversion element has a circular shape.

22. The photon engine of claim 19, wherein an inner surface of the reflective optical cavity has a paraboloidal shape.

23. The photon engine of claim 19, wherein an inner surface of the reflective optical cavity has an elliptical shape.

24. The photon engine of claim 19, wherein an inner surface of the reflective optical cavity has a specular reflectivity.

25. The photon engine of claim 19, wherein an inner surface of the reflective optical cavity has a diffuse reflectivity.

26. The photon engine of claim 19, wherein the primary excitation source comprises at least one light-emitting diode (LED).

27. The photon engine of claim 26, wherein the at least one LED is configured to emit electromagnetic radiation at the first peak wavelength, wherein the first peak wavelength falls in the range of about 365 nm to about 465 nm.

28. The photon engine of claim 26, wherein the secondary emitter conversion element is configured to emit electromagnetic radiation at the second peak wavelength, wherein the second peak wavelength falls in the range of about 415 nm to about 705 nm.

29. The photon engine of claim 19, comprising a material disposed in the gap.

30. The photon engine of claim 29, wherein the material is optical grade Silicone.

31. The photon engine of claim 19, comprising a substrate to receive the primary excitation source, wherein the substrate comprises a reflective surface.

32. The photon engine of claim 31, wherein the reflective surface reflects the electromagnetic radiation at the second peak wavelength back into an input surface of the secondary emitter conversion element.

33. A light source, comprising:
a primary excitation source configured to emit electromagnetic radiation at a first peak wavelength and a band of wavelengths around the first peak wavelength;
a secondary emitter conversion element optically coupled to the primary excitation source, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
a non-imaging optical coupler optically coupled to the secondary emitter conversion element;
a gap between the secondary emitter conversion element and the non-imaging optical coupler; and
a material disposed in the gap.

34. The light source of claim 33, wherein the secondary emitter conversion element comprises a phosphor material.

35. The light source of claim 33, comprising:
a reflective optical cavity configured to receive the secondary emitter conversion element.

36. The light source of claim 35, wherein the reflective optical cavity comprises a seat to receive the secondary emitter conversion element.

37. The light source of claim 35, wherein the reflective optical cavity has a cylindrical shape and the secondary emitter conversion element has a circular shape.

38. The light source of claim 35, wherein an inner surface of the reflective optical cavity has a paraboloidal shape.

39. The light source of claim 35, wherein an inner surface of the reflective optical cavity has an elliptical shape.

40. The light source of claim 35, wherein an inner surface of the reflective optical cavity has a specular reflectivity.

41. The light source of claim 35, wherein an inner surface of the reflective optical cavity has a diffuse reflectivity.

42. The light source of claim 33, comprising:
a substrate to receive the primary excitation source, wherein the substrate comprises a reflective surface; and
a heat transfer element thermally coupled to the substrate.

43. The light source of claim 33, wherein the primary excitation source comprises at least one light-emitting diode (LED).

44. The light source of claim 43, wherein the at least one LED is configured to emit electromagnetic radiation at the first peak wavelength, wherein the first peak wavelength falls in the range of about 365 nm to about 465 nm.

45. The light source of claim 43, wherein the secondary emitter conversion element is configured to emit electromagnetic radiation at the second peak wavelength, wherein the second peak wavelength falls in the range of about 415 nm to about 705 nm.

46. The light source of claim 33, wherein the material is optical grade Silicone.

47. An optical system, comprising:
a light source; and
a transparent rod optically coupled to the light source;
wherein the light source comprises:
a primary excitation source configured to emit electromagnetic radiation at a first peak wavelength and a band of wavelengths around the first peak wavelength;
a secondary emitter conversion element optically coupled to the primary excitation source, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
a non-imaging optical coupler optically coupled to the secondary emitter conversion element;
a gap between the secondary emitter conversion element and the non-imaging optical coupler; and
a material disposed in the gap.

48. The optical system of claim 47, wherein the secondary emitter conversion element comprises a phosphor material.

49. The optical system of claim 47, comprising:
a reflective optical cavity configured to receive the secondary emitter conversion element.

50. A photon engine, comprising:
a primary excitation source configured to emit electromagnetic radiation at a first peak wavelength and a band of wavelengths around the first peak wavelength;
a secondary emitter conversion element optically coupled to the primary excitation source, the secondary emitter conversion element comprising a phosphor material, the secondary emitter conversion element configured to absorb at least a portion the electromagnetic radiation at the first peak wavelength from the primary excitation source and emit electromagnetic radiation at a second peak wavelength and a band of wavelengths around the second peak wavelength, wherein the second peak wavelength is longer than the first peak wavelength;
a reflective optical cavity configured to receive the secondary emitter conversion element;
a heat transfer element thermally coupled to the primary excitation source;
a non-imaging optical coupler optically coupled to the secondary emitter conversion element;
a gap between the secondary emitter conversion element and the non-imaging optical coupler; and
a material disposed in the gap.

51. The photon engine of claim 50, wherein the reflective optical cavity comprises a seat to receive the secondary emitter conversion element.

52. The photon engine of claim 50, wherein the reflective optical cavity has a cylindrical shape and the secondary emitter conversion element has a circular shape.

53. The photon engine of claim 50, wherein an inner surface of the reflective optical cavity has a paraboloidal shape.

54. The photon engine of claim 50, wherein an inner surface of the reflective optical cavity has an elliptical shape.

55. The photon engine of claim 50, wherein an inner surface of the reflective optical cavity has a specular reflectivity.

56. The photon engine of claim 50, wherein an inner surface of the reflective optical cavity has a diffuse reflectivity.

57. The photon engine of claim 50, wherein the primary excitation source comprises at least one light-emitting diode (LED).

58. The photon engine of claim 57, wherein the at least one LED is configured to emit electromagnetic radiation at the first peak wavelength, wherein the first peak wavelength falls in the range of about 365 nm to about 465 nm.

59. The photon engine of claim 57, wherein the secondary emitter conversion element is configured to emit electromagnetic radiation at the second peak wavelength, wherein the second peak wavelength falls in the range of about 415 nm to about 705 nm.

60. The photon engine of claim 59, wherein the material is optical grade Silicone.

61. The photon engine of claim 50, comprising a substrate to receive the primary excitation source, wherein the substrate comprises a reflective surface.

62. The photon engine of claim 61, wherein the reflective surface reflects the electromagnetic radiation at the second peak wavelength back into an input surface of the secondary emitter conversion element.

* * * * *